United States Patent [19]

McNamara et al.

[11] Patent Number: 4,711,851
[45] Date of Patent: Dec. 8, 1987

[54] TEST APPARATUS FOR DETERMINING A METABOLIC CHARACTERISTIC OF MICROORGANISMS

[75] Inventors: Thomas F. McNamara, Port Jefferson; Fred Confessore, St. James, both of N.Y.

[73] Assignee: State University of New York, Albany, N.Y.

[21] Appl. No.: 612,462

[22] Filed: May 21, 1984

[51] Int. Cl.$^4$ ............................................. C12M 1/00
[52] U.S. Cl. .................................... 435/287; 435/289; 435/290; 435/291; 422/63
[58] Field of Search .............. 435/287, 289, 290, 291, 435/316; 422/63, 64, 65, 66, 67, 68

[56] References Cited

U.S. PATENT DOCUMENTS

| | | | |
|---|---|---|---|
| 3,765,237 | 10/1973 | Blachmer et al. | 435/290 |
| 3,773,426 | 11/1973 | Mudd | 435/291 |
| 3,878,049 | 4/1975 | Tannenbaum et al. | 438/291 |
| 3,926,737 | 12/1975 | Wilson et al. | 435/290 |
| 4,048,040 | 9/1977 | Schwartz | 422/68 |
| 4,090,921 | 5/1978 | Sawamura et al. | 435/290 |
| 4,204,037 | 5/1980 | Dill et al. | 435/289 |
| 4,338,280 | 7/1982 | Ambers et al. | 422/68 |
| 4,359,447 | 11/1982 | Welch | 422/67 |
| 4,367,043 | 1/1983 | Sweet et al. | 435/291 |
| 4,383,041 | 5/1983 | Kutsusawa et al. | 435/291 |
| 4,424,559 | 1/1984 | Lorincz et al. | 435/290 |
| 4,429,584 | 2/1984 | Beyer et al. | 422/67 |
| 4,487,836 | 12/1984 | Takayaragi et al. | 422/68 |
| 4,512,852 | 4/1985 | Tsuboshima et al. | 422/67 |
| 4,513,280 | 4/1985 | Hannan et al. | 435/291 |
| 4,576,916 | 3/1986 | Lowhe | 435/289 |
| 4,598,049 | 7/1986 | Zelinha et al. | 435/289 |

*Primary Examiner*—Samuel Scott
*Assistant Examiner*—H. A. Odar
*Attorney, Agent, or Firm*—Omri M. Behr

[57] ABSTRACT

A tester can determine a metabolic characteristic of a microorganism suspended in a medium. The tester has a reagent supply, a probe, a dispenser and a controller. The reagent supply contains a quantity of at least one test reagent. The probe is sized to be inserted into the medium and for providing a reaction signal signifying the temperature of a fluid at the probe means. The dispenser is coupled between the reagent supply and the probe for delivering at the latter from the former a controllable amount of test reagent. The controller is coupled to the probe and to the dispenser for controlling the amount of test reagent dispensed by the dispenser and recording the variation of the reaction signal after delivery of the test reagent.

19 Claims, 10 Drawing Figures

TEST APPARATUS FOR DETERMINING A METABOLIC CHARACTERISTIC OF MICROORGANISMS

BACKGROUND OF THE INVENTION

The copending application filed simultaneously herewith and entitled "Identification of Metabolic Characteristics of Microorganisms", is incorporated herein by reference.

The present invention relates to test apparatus for determining a metabolic characteristic of a microorganism suspended in a medium.

The above copending patent application describes how several test tubes or other containers can be inserted into a hollow holder. The holder can be filled with a temperature stabilizing liquid that is thermally regulated so that the test tubes placed in the holder all reach the same equilibrium temperature. This copending application describes a method for placing microorganisms suspended in a medium in one of the test tubes. A reagent which may inhibit or enhance microorganism growth is placed in another one of the test tubes within the holder. In addition, a central test tube is filled with a washing fluid. Two temperature probes can be inserted, one into the microorganism-containing medium, the other in the reagent. After thermal equilibrium is reached, a quantity of reagent is transferred to the medium containing the microorganism. After an interval of time, any change of temperature caused by an alteration in the metabolic rate of the microorganism is recorded. Since two probes are used, a differential temperature can be measured. This approach is highly immune to common thermal affects that may effect both tubes identically. The central tube containing a washing fluid can be used to initially balance the instrument and can be used between tests to clean the probe tips.

It is known to use certain equipment in electronic instrumentation. For example, a Wheatstone bridge, as well as a differential amplifier is well known in the instrumentation art. It is also known to build an incubator having hollow walls filled with water whose temperature is regulated.

Accordingly, there is a need for providing apparatus which can perform test of the foregoing type so that a rapid and accurate measurement can be made of metabolic characteristics.

SUMMARY OF THE INVENTION

In accordance with the illustrative embodiments demonstrating features and advantages of the present invention, there is provided a tester for determining a metabolic characteristic of microorganisms suspended in a medium. The tester has a reagent supply containing a quantity of at least one test reagent. Also included is a probe means sized to be inserted into the medium and for providing a reaction signal signifying the temperature of fluid at the probe means. The tester has a dispensing means coupled between the reagent supply and the probe means for delivering at the latter from the former, a controllable amount of the test reagent. Also included is a control means coupled to the probe means and the dispensing means for controlling the amount of test reagent dispensed by the dispensing means and recording the variation of the reaction signal after delivery of the test reagent.

In another embodiment of the same invention, a tester for determining the effect caused by a test reagent on a metabolic characteristic of a microorganism suspended in a medium, includes a reaction container containing the medium. Also included is a reagent container containing the test reagent. The tester has an equilibrating means for commonly stabilizing the temperatures within the reaction and reagent containers. Also included is a probe means for providing a reaction signal signifying the variation in temperature in said reaction container. Thus, the probe means can determine a temperature change caused by a transfer of a portion of the test reagent in the reagent container to the reaction container.

By employing equipment of the foregoing type, a highly efficient and accurate test apparatus is provided. In one embodiment of the invention an array of test samples is enclosed in a water jacketed housing. The array of samples may be mounted on a platform that can be moved in two directions, horizontally and vertically. A row of reaction sensors can be aligned with the columns of samples so that successive rows of samples can immerse each one of the reaction sensors.

In this embodiment, the reagent is provided from a plurality of reservoirs fed to individual reaction sensors by respective pumps or regulators. Each reaction probe also has connected to it a wash tube for supplying a washing fluid to cleanse the reaction probe between tests.

A preferred embodiment employs a microprocessor which verifies the temperature in the water jacket and in the chamber as well as the temperature of the reagent and wash fluid. If the temperatures are within an acceptable range, the microprocessor moves the platform to allow successive temperature measurements of the samples after reagent is injected into them. The resulting temperature change can be printed out to indicate a metabolic characteristic of the microorganism.

In another embodiment, a pair of probes can be used to test an individual sample and reagent. These two sensors can be connected as separate branches in a Wheatstone bridge having two opposing nodes connected to a differential amplifier. This configuration is highly stable since common thermal disturbances are nulled. This type of equipment can be also coupled with an injection pump for delivering reagent to the test sample and with a wash pump for cleansing the probe after testing. In some embodiments this probe can be used manually to rapidly perform the sequence of steps necessary to determine metabolic characteristics of a microorganism.

BRIEF DESCRIPTION OF THE DRAWING

The above brief description as well as other features and advantages of the present invention will be more fully appreciated by reference to the following detailed description of a presently preferred but nonetheless illustrative embodiment in accordance with the present invention when taken in conjunction with the accompanying drawings, wherein.

DETAILED DESCRIPTION OF THE PREFERRED EMBODIMENTS

Figures 1, 3:
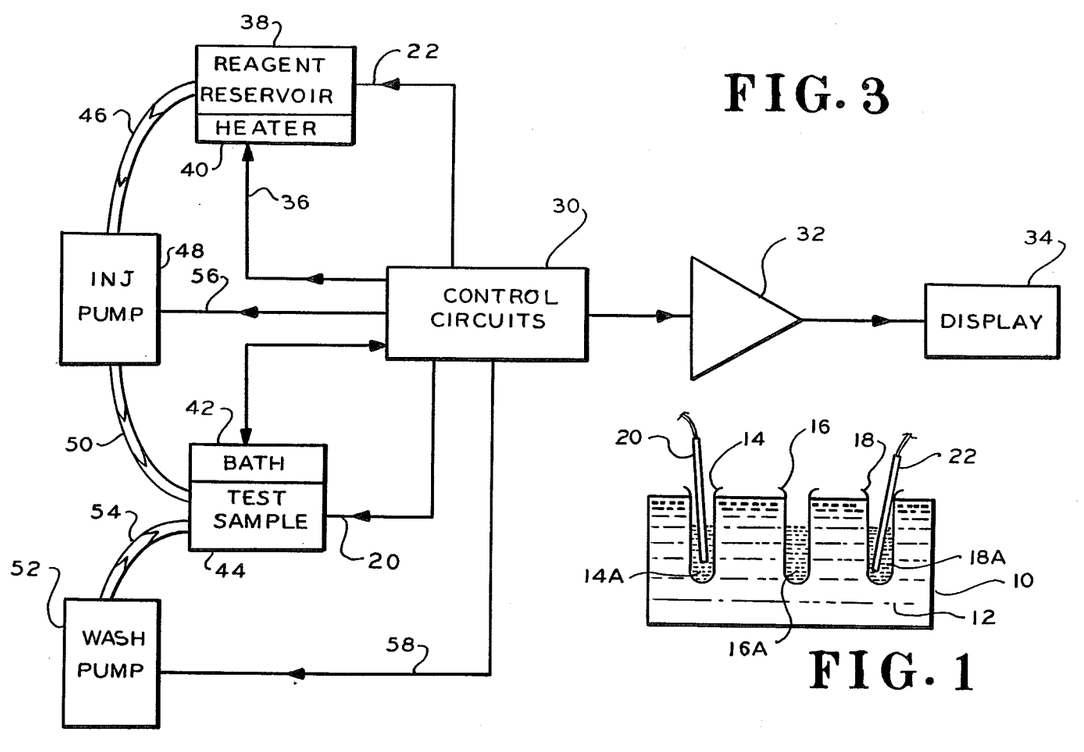
FIG. 1 is a schematic, sectional and elevational view of a test apparatus as disclosed in the above mentioned copending patent application.
FIG. 3 is a block diagram of a tester according to the principles of the present invention.

FIG. 1 is a highly simplified illustration of the apparatus disclosed in the above noted copending patent application. Container 10 is filled with liquid 12, which liquid may be temperature regulated. Mounted in upper apertures of container 10 are test tubes 14, 16 and 18. The tube 14 contains a medium 14A in which are suspended microorganisms. Test tube 16 contains a washing fluid 16A such as distilled water. Test tube 18 may contain a reagent 18A as disclosed in the above noted copending patent application. For example, reagent 18A may be sorbitol, mannitol, sucrose, xylose, arginine, lactose, citrate, roffinose, inositol, arabinose or urea. The foregoing are reagents which may induce growth of a microorganism depending upon its type. Alternatively, the reagent 18A can be a potentially growth inhibiting antibiotic, for example, bacitracin or kanamycin. The foregoing list of reagents is merely examplary and other reagents will be used depending upon the suspected microorganisms or the type of sensitivity test being performed. Typically, the microorganism to be identified or tested is grown up in broth, centrifuged and the resulting pellet is resuspended in a medium (e.g. distilled water) free of both growth enhancing or inhibiting agents. Alternatively, microorganisms can be harvested from agarplates and resuspended, for example, in distilled water.

The apparatus of FIG. 1 is shown with a probe means 20 and a reference means 22. As will be further described hereinafter, elements 20 and 22 are essentially temperature sensors that can be used to determine the temperature in the respective test tubes.

Figure 2:
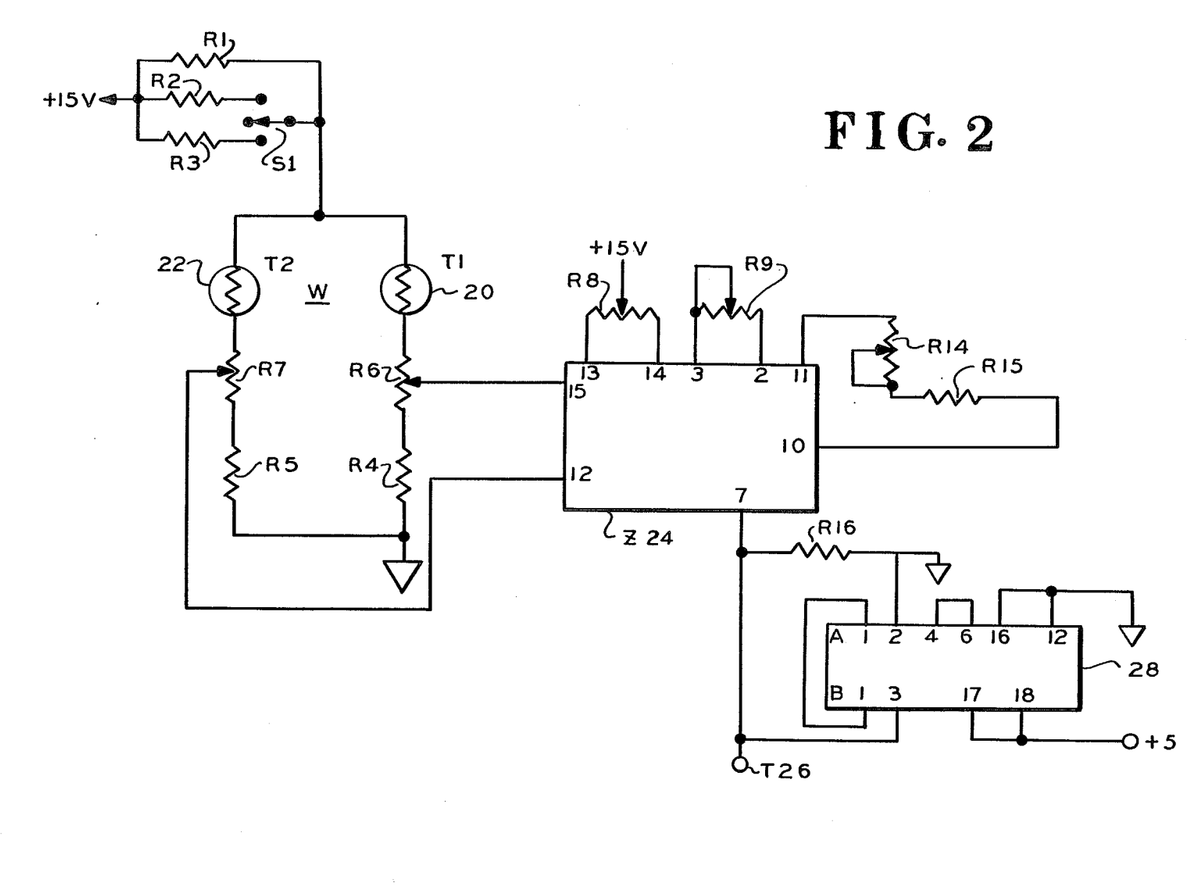
FIG. 2 is a schematic diagram of a differential means connected to a reference means and probe means that may be employed in the present invention.

Referring to FIG. 2, this electronic schematic shows circuitry for measuring the voltages produced by the probes 20 and 22, previously mentioned in FIG. 1. In this embodiment, both the probe means 20 and the reference means 22 are shown as thermistors having a structure described in further detail hereinafter. Each of the sensors 20 and 22 are a pair of matched thermistors type GB32PM122 manufactured by Fenwall of Framingham, Mass., although clearly, other thermistors, thermocouples, semi-conductor temperature sensors or equivilent devices can be used instead. Thermistors 20 and 22 have a common terminal connected to resistor R1 whose other terminal is connected to a +15 volt supply. The junction of thermistors 20 and 22 is also connected to the wiper of three position rotary switch S1 which can select one terminal of either resistor R2 or R3 whose other terminals are connected in common to +15 volts. Thermistor 22 is connected in series through the resistive element of potentiometer R7 and with resistor R5 to ground. Similarly, thermistor 20 is connected in series through the resistive element of potentiometer R6 and resistor R4 also to ground. Thus connected, thermistors 20 and 22 are part of a Wheatstone bridge for producing a null across the wipers of potentiometer R6 and R7 when in balance. The wipers of potentiometers R6 and R7 connect to the differential inputs of a differential means, conditioning circuit Z24. Circuit Z24 includes a differential amplifier with adjustable gain and offset. In a preferred embodiment, circuit Z24 was an integrated circuit package type 2B30L manufactured by Analog Devices, USA. An offset adjustment is set into circuit Z24 by potentiometer R8 connected between pins 13 and 14 with its wiper connected to +15 volts. Fine gain adjustment is provided by variable resistor R9 connected across pins 2 and 3 of circuit Z24. Coarse gain is provided by resistor R15 serially connected with variable resistance R14 across pins 10 and 11. It will be understood that in some embodiments resistors R14 and 15 can be controlled by range switches to significantly change their effective value. A conditioned signal is issued on pin 7 to output terminal T26. The output on terminal T26 is also connected to the input 3 of digital voltmeter 28 for displaying the differential reading produced by the test. In one constructed embodiment, voltmeter 28 was a digital panel meter type DM4100L manufactured by Datel Intersil. However, it will be appreciated that alternate voltmeters can be used and in some embodiments no voltmeter will be employed. Furthermore, in some automated embodiments, the meter may provide a data output to produce computer readable measurements.

The circuit of FIG. 2 can be operated after the samples, reagents and wash fluid are set-up as illustrated in FIG. 1. Thereafter, elements 20 and 22 can be placed into the sample test tube 14 and reagent test tube 18, respectively. Once reagent is transferred to sample test tube 14, a temperature change may occur. Under these circumstances, the resulting difference in resistance between thermistors 20 and 22 causes an imbalance of the bridge W, resulting in a differential voltage across inputs 15 and 12 of integrated circuit Z24.

Initially, the instrument can be balanced by placing both thermistors 20 and 22 in the wash test tube 16 (FIG. 1). Thereafter, the potentiometers R6 and R7 can be adjusted to cause a null. The sensitivity of the bridge W can be adjusted by switch S1. Also, the gain and offset of the circuit of Z24 can be adjusted through potentiometers R8, R9 and R14 to produce a calibrated reading from digital voltmeter 28 in, for example, C° or F°.

Depending upon the microorganism and in dependence upon the reagent used (whether it be a weak or potent growth inducing or inhibiting substance) the voltage change measured by voltmeter 28 will vary. The amount of change and the time required for the change will also depend as noted above. The user can simply establish these parameters by working with a known microorganism and a known reagent to determine in advance the results to be expected from these controlled conditions.

Referring to FIG. 3, an alternate tester is disclosed which again uses a reference probe 22 and a reaction probe means 20. In this embodiment these two probes 20 and 22 are connected to a control means 30 which contains the bridge circuit illustrated in FIG. 2. The differential amplifier and digital voltmeter of FIG. 2 are shown herein as amplifier 32 and display 34, respectively. Control means 30 also includes additional equipment. It includes a conventional thermostatic loop in which the temperature signals sensed by reference probe 22 is used to control the heater 40 driven by line 36 from controller 30. In this embodiment probe 22 is inserted into a large reagent supply 38. This may be a large supply of the previously noted reagents. A selector valve (not shown) can be used to select any one of several desired reagents. Probe 22 is thus inserted into one such reagent supply to provide a feedback signal to the control circuit 30 to regulate the amount of drive to heater 40. In a preferred embodiment, the heater 40 is either on or off depending upon whether the probe 22 detects the reservoir temperature being above or below a desired temperature.

In this embodiment a similar thermostatic control loop is provided for a bath 42 that encompass the test sample 44. For example, a structure similar to that of FIG. 1 can be employed but wherein a heater coil and a temperature sensor is contained within the bath water to keep it at a regulated temperature. In this embodiment, it is important that the reagent heater 40 and the bath heater 42 are regulated so that the reagent 38 and test sample 44 are kept at about the same temperature. The reagent reservoir 38 can supply reagent through cannula 46 to a dispensing means 48 in the form of an injection pump. Various pumps can be employed in dispensing means 48. For example: a Series 2 micropump by Ace Industrial Division, Linden, N.J.; peristaltic pumps by Gilson, Middleton, Wis.; metering pumps (Catalog 115B) by Tuttle, of Chicago, Ill.; Lambda Pump Model 1302 by Harvard Apparatus of Massachusetts; Ismatec Peristaltic Pumps by Brinkman Instruments of Westbury, N.Y.; or Masterflex Pumps by Barnant Corp. of Barrington, Ill.

The discharge of pump 48 is fed through cannula 50 to the test sample 44 to allow mixing of reagent with the medium containing the microorganism. A wash supply and purge means 52 has a supply of distilled water delivered through cannula 54 by an internal pump similar to pump 48. Cannula 54 is also placed adjacent the test sample 44 to allow washing of probe 20 when it is removed.

Pumps 48 and 52 are also controlled by control means 30. Control means 30 includes manually operable timers; for example, one shot multivibrators (not shown) that may be manually triggered by a push button switch. These timer circuits are used to produce control signals on lines 56 and 58 to energize for a predetermined period of time pumps 48 and 52, respectively.

In operation, the user of the equipment of FIG. 3 would initially prepare a test tube containing a microorganism suspended in an appropriate medium and place the test sample 44 in the bath 42. Thereafter, the cannula 50 may positioned to feed test sample 44, cannula 54 also remaining in the vicinity. In some embodiments, cannula 50 and 54 may be mounted directly on the probe 22 so that they will be inserted together.

Thereafter, the operator will balance and adjust the gain of the differential circuits in control means 30 as described for FIG 2. It may be necessary to wait a period of time to allow the temperatures in test sample 44 to stabilize. A stable reading will indicate that the heaters 40 and 42 are operating to produce stable temperatures in the reagent reservoir 38 and in the test sample 44. Once such equilibrium has been reached, the user may manually energize pump 48 which will operate for a length of time sufficient to dispense a predetermined amount of reagent from reservoir 38 into test sample 44. Thereafter, the operator will observe the display 34 to see how the reading may change as a result of reagent injection. Once the reading has been recorded, probe 20 and cannulas 50 and 54 may be removed. The operator may now manually initiate purge mean 52 to produce a flow of distilled water across probe 20. This describes a cycle which now may be repeated to test a different test sample. Before starting this new cycle, a new reagent reservoir may be substituted for reservoir 38 or a selector valve (not shown) may be used to select a different type of reagent.

Figures 4A, 4B:
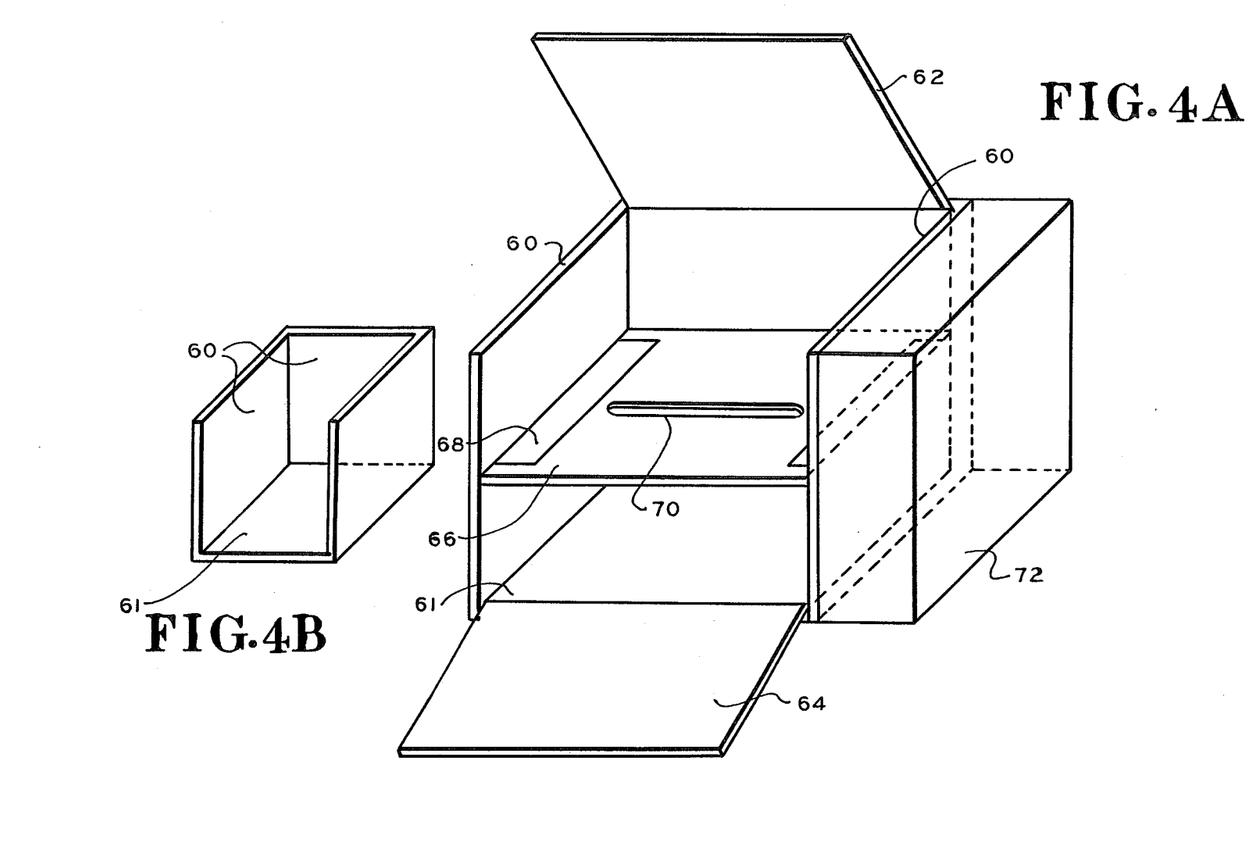
FIG. 4A is a perspective view of a housing that may be used with the apparatus of the present invention.
FIG. 4B is a detail of a component employed in the housing of FIG. 4A.

If it is desired to perform tests of the foregoing type automatically with a large number of samples under test, it is important to have a temperature controlled environment so that the various reagents and test samples can reach equilibrium. The housing shown in FIGS. 4A and 4B is designed for this purpose. FIG. 4B shows a rectangular, four sided box, open at the top and front. This structure employs type of hollow panels 60, 61 containing water regulated to a desired temperature. This structure is similar to available incubators, for example, incubators manufactured by Forma Scientific Co. This stucture is shown in a more finished form in FIG. 4A wherein lid 62 is hinged at the top of rear wall 60 and front cover 64 is hinged at the front of floor 60. Horizontal shelf 66 is mounted between the three vertical walls 60 and is supported by channels 68. Shelf 66 has a slot 70 through which probes may be inserted in a manner to be described hereinafter. A hollow rectangular cabinet 72 is mounted on the right side of the housing as a location where the electronics described hereinafter may be contained.

Figure 5:
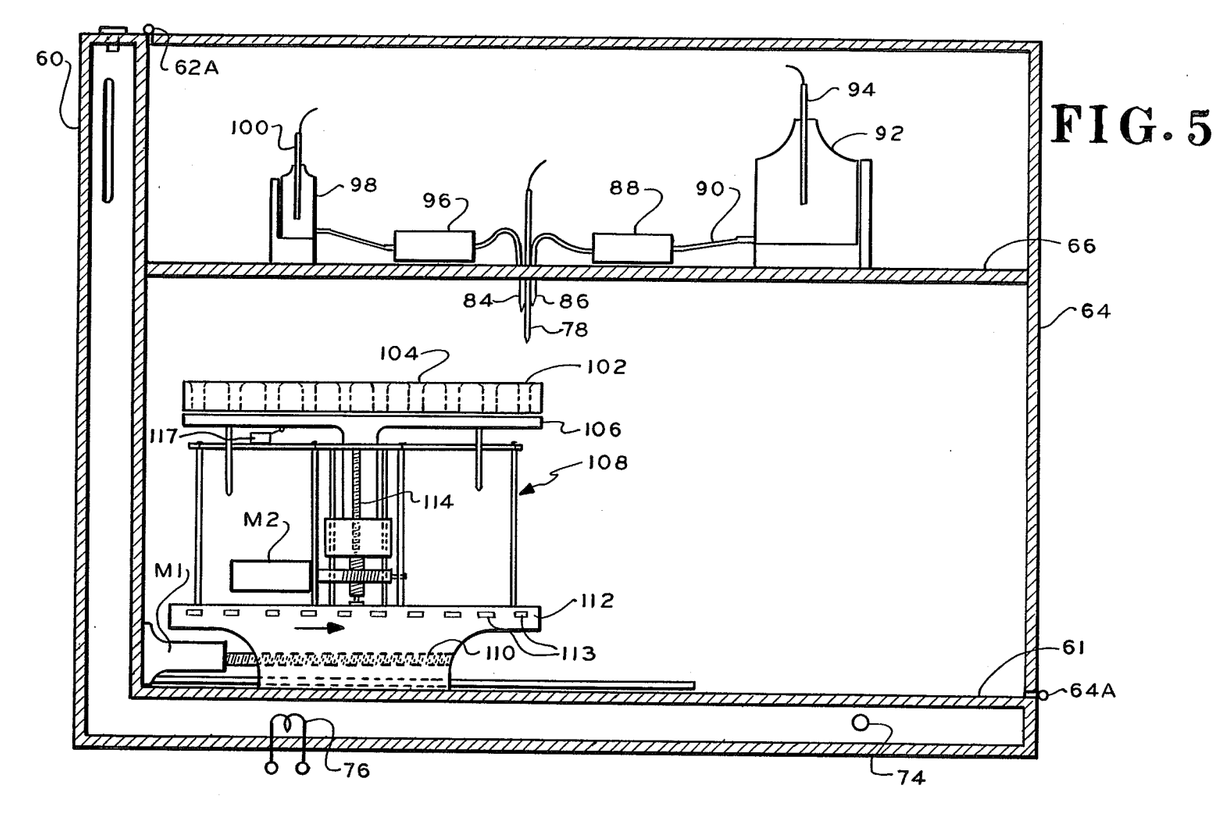
FIG. 5 is a sectional, side view of an alternate tester according to the principles of the present invention.
Figure 6:
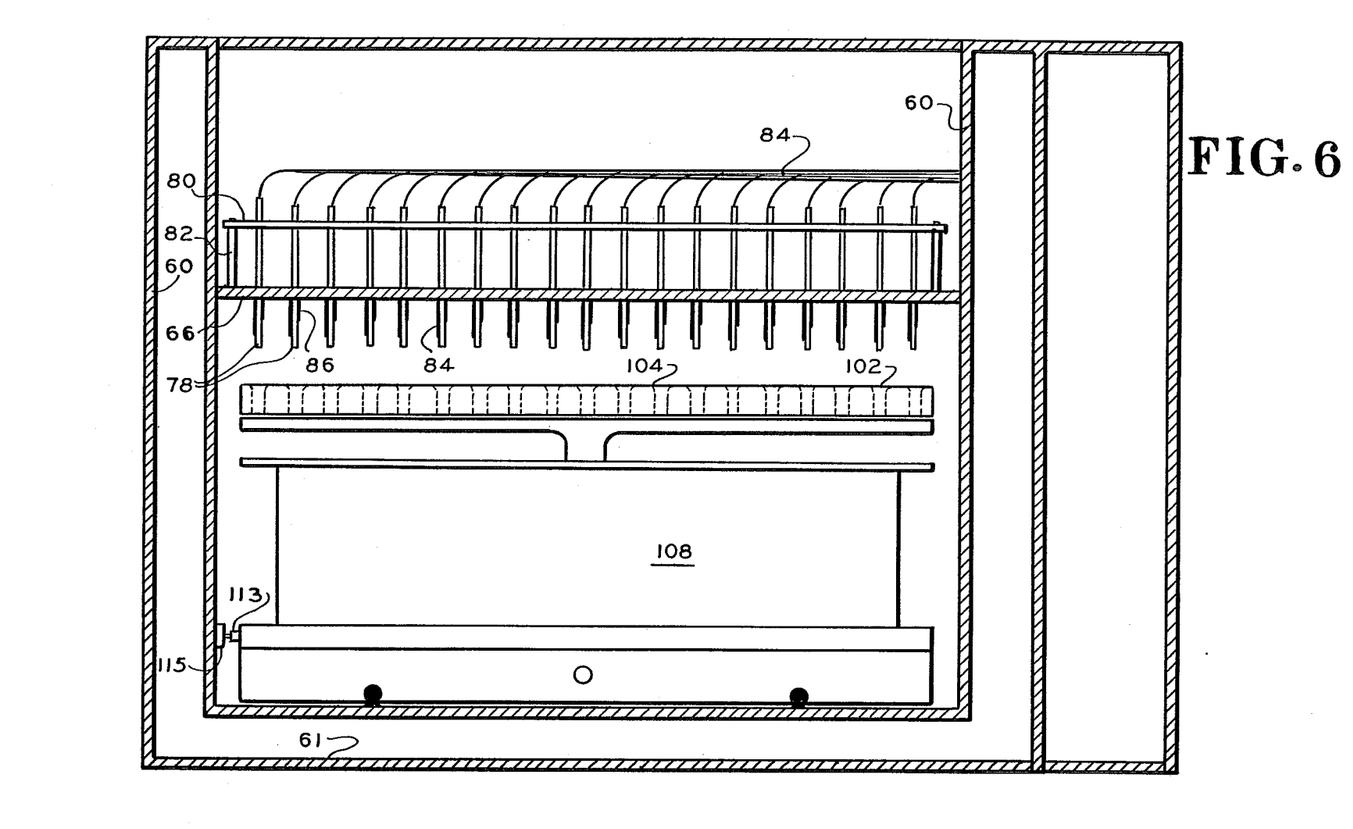
FIG. 6 is a sectional, front view of the tester of FIG. 5.

Referring to FIGS. 5 and 6, the previously described housing is shown containing a tester according to the present invention. In this view, hollow jackets 60 and 61 are shown to freely intercommunicate. Clearly visible in this view are hinges 62A and 64A which provide a pivot point for panels 62 and 64, respectively.

Illustrated in FIG. 5, but only schematically, is reference means 74 which is a conventional temperature sensor for monitoring the temperature of the fluid within hollow panels and 61. Sensor 74 may be connected in a thermostatic loop to schematically illustrated heater coil 76 so that the temperature of water within the hollow panels 60 and 61 is kept at a predetermined constant. In FIG. 6, nineteen reaction sensors are shown arranged side by side through the previously described slot in shelf 66. The reaction sensors 78 may be constructed similarly to the probe means described in FIG. 2. The sensors 78 are supported at their upper end by an apertured rack 80 mounted on a pair of upright studs 82 at either end of the rack 80. The twisted pair from each sensor 78 is bundled into a cable 84 to connect to the electronics described hereinafter. As shown in FIG. 5, the reaction sensor 78 is positioned between reagent tube 84 and wash tube 86. Tube 86 is fed by purge means 88, a pump similar to the injection pump 52 described in FIG. 3. Pump 88 is fed by a tube 90 leading from a lower outlet in a wash supply bottle 92 filled with distilled water or other appropriate washing fluid. Mounted through the neck of bottle 92 for monitoring the temperature of wash fluid is a reference means 94 which is identical to the reaction sensor 78. Tube 84 is connected to the discharge of pump 96, a pump similar to pump 88. The inlet of pump 96 is connected to a lower port of a reagent supply in the form of reservoir 98. A reagent sensor 100 similar to sensor 94 is also mounted in the neck of reservoir 98.

It is to be understood that in this embodiment, there is one pump (regulator) 96 and reagent container 98 for each of the plurality of tubes 84. In this embodiment nineteen tubes are provided, one for each reaction sensor 78 (FIG. 6). While there may also be a plurality of purge means 88, preferably only one larger pump may have its discharge connected in parallel to each wash tube 86 so that one pump serves each station.

Each of the probes 78 are aligned with one reaction container 102 (FIG. 6) in the row of reaction containers. In this disclosed embodiment, there is a tray 104 having a plurality of depressions arranged in rows and columns to receive the reaction containers (or test tubes) 102 that are placed in these depressions. The rack 104 is rests on a platform 106 of a positioning means 108. Positioning means 108 employs a motor driven lead screw 110 (motor M1) for driving the frame 112 in a horizontal direction, that is, front to back. Another motor driven lead screw 114 (motor M2) can vertically reciprocate platform 106. The positioning means 108 may be custom built or may be a purchased assembly by Velmex, Inc. of New York, selected from their Unislide Motor Driven Assemblies line, for example, catalog M-76 and-/or catalog G-76. In some embodiments the motors M1 and M2 driving the lead screws 110 and 114 may be stepper motors, in which case, a stepper motor controller can be used, for example, a type CY500 manufactured by Cybernetic Microsystems of California. Alternatively, a DC motor can be employed and can be controlled by conventional techniques. Another possible embodiment can provide vertical translation through a motorized vertical translator such as those manufactured by Oriel Corporation of Stamford, Conn. The freedom of motion obtainable by positioning means 108 is sufficient to raise platform 106, immerse probe 78 into reaction container 102 and then remove the probe. Platform 106 is also horizontally movable to allow probe 78 access to the first and last reaction container 102 in the column.

The positioning means 108 could be controlled by resolvers feeding back the actual position to a servomotor. However, it is preferred to employ limit switches 115 and 117. Switch 117 is a microswitch mounted below platform 106 to sense its vertical motion when platform reaches the proper height for performing a measurement of sample temperature, switch 117 is actuated. A series of eleven stops 113 (FIG. 5) are arranged in a horizontal column on the side of frame 112. As seen best in FIG. 6, stops 113 sequentially engage microswitch 115 to provide a signal when probes 78 are aligned (front to back) with the samples 102.

Figures 7, 9:
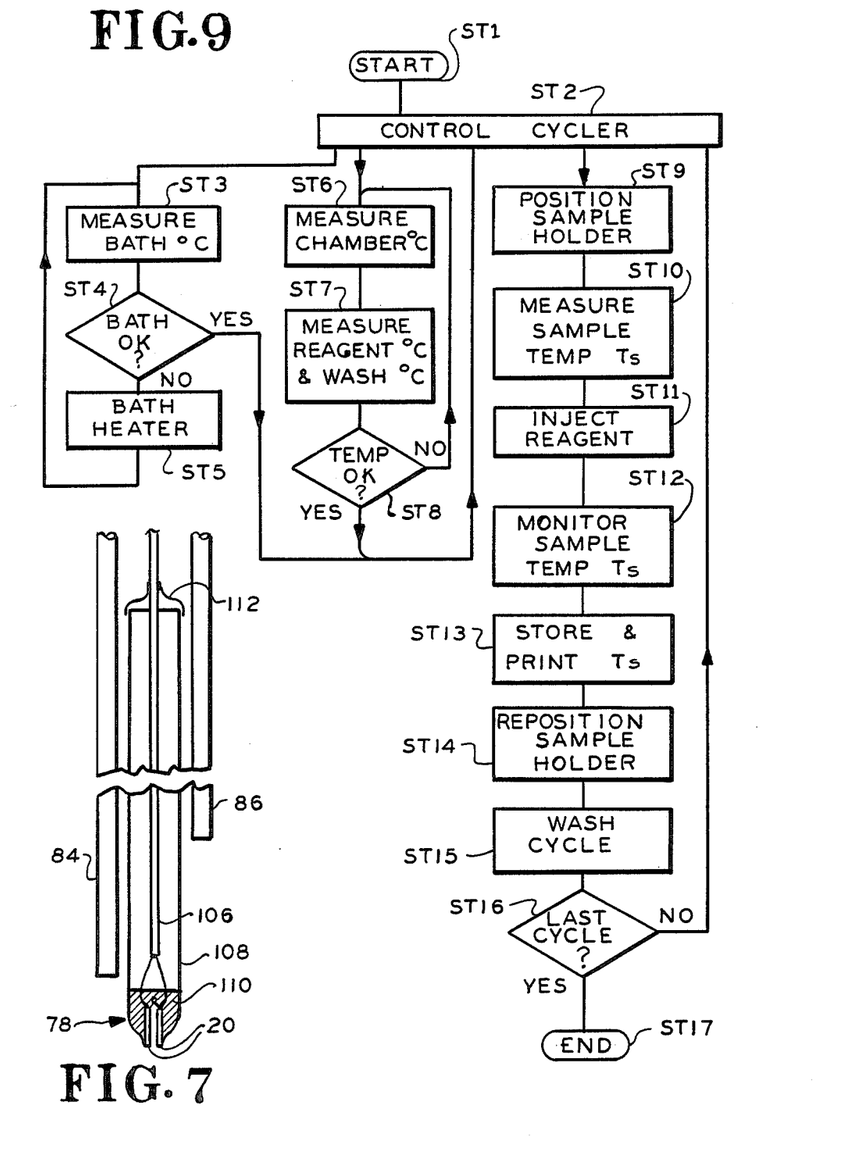
FIG. 7 is a longitudinal, sectional view of the probe means and the associated tubes employed in the apparatus of FIG. 5.
FIG. 9 is a flow chart showing the nature of the program associated with the processor of FIG. 8.

Referring to FIG. 7, a longitudinal sectional view is given of the previously mentioned probe means. Thermistors 20 are the previously mentioned type GB32PM122 iso-curve thermistors manufactured by Fenwall in housing type H35 or 36. Alternatively, a series S10 type thermistor manufactured by Thermometrics can be used instead. Thermistors 20 are as a pair of thermistors connected in series to the two leads of twisted pair 106. Thermistors 20 ae mounted within a 6" long ¼" diameter glass tube whose lower mouth is heat reduced to a relatively small opening. Thermistors 20 are sealed into this mouth in epoxy base 110. The upper end of tube 108 is sealed by a heat shrink sleeve 112. Mounted alongside tube 108 are previously mentioned reagent tube 84 and ash tube 86. In some embodiments, the tubes 108, 84 and 86 may be strapped together by a larger heat shrink tube or by other means to keep all three bound together. Alternatively, each may be separately mounted in a corresponding hole in a single frame.

Figure 8:
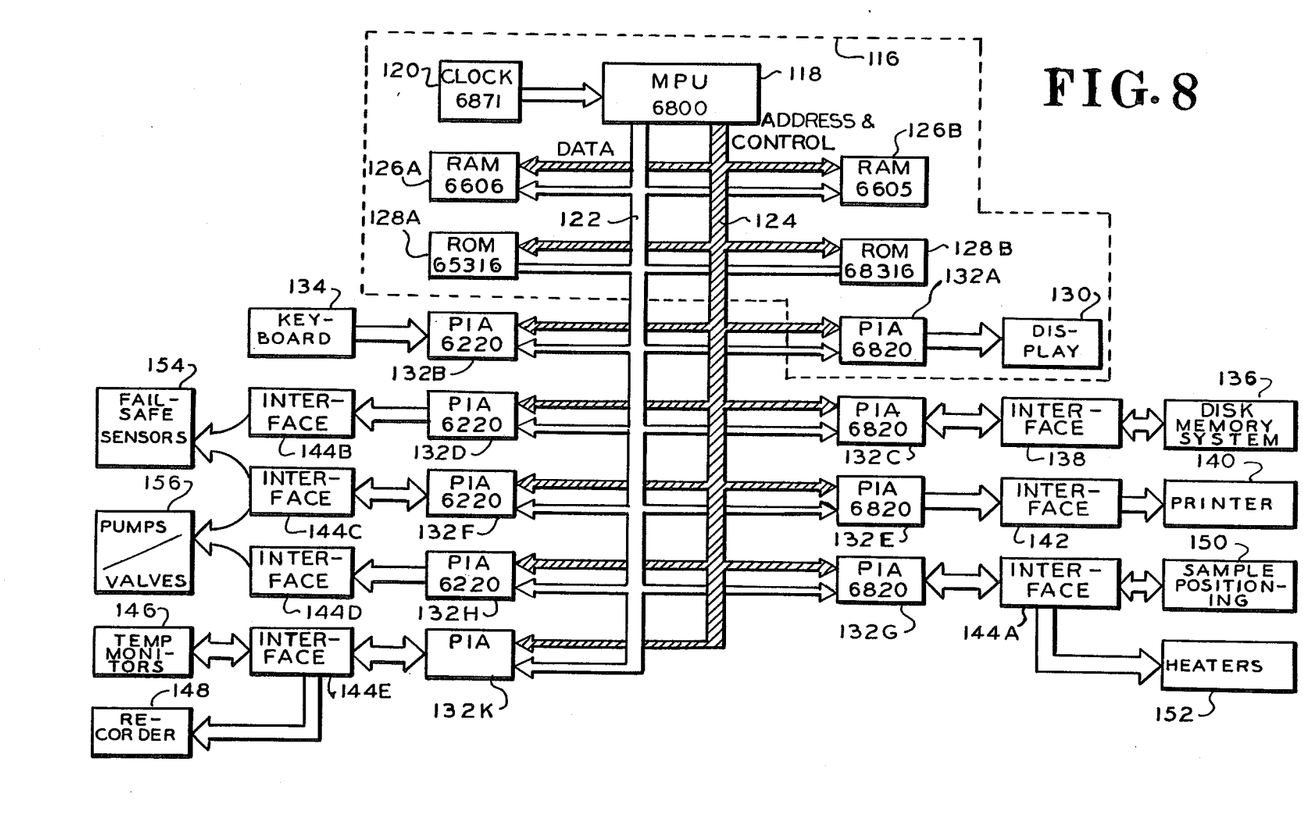
FIG. 8 is block diagram of the electronic hardware used with the apparatus of FIG. 5.

Referring to FIG. 8, a control means is shown within block 116. Control means 116 includes a digital processor 118 in the form of a type 6800, eight-bit microprocessor manufactured by Motorola. Microprocessor 118 is shown connected to a timing clock 120 which may be, for example, a type 6871 timing clock manufactured by Motorola. Microprocessor 118 has a data bus 122 and an address and control bus 124. Buses 122 and 124 connect to respective ports on random access memories 126A and 126B as well as read only memories 128A and 128B. Memories 126A and 126B may be integrated circuit type 6605 manufactured by Motorola. Memories 128A and 128B may be integrated circuit type 68316 also manufactured by Motorola.

Display 130 may be an alpha numeric display or a cathode ray tube (CRT). For example, the monitors normally associated with a personal computer can be employed as a display 130. Display 130 is driven by a peripheral interface adapter 132A which is arranged to interface with bus lines 122 and 124. Adapter 132A can be a controllable buffer with registers arranged in the usual fashion to exchange data between a microcomputer and a peripheral device. In one emodiment, adapter 132A was an MOS integrated circuit type MC6820 manufactured by Motorola, although, other integrated circuits may be used instead. In this embodiment, adapters 132A–132K are identical integrated circuits each having their respective address and data ports connected to buses 122 and 124. Thus arranged, adapters 132A–132K can exchange data between their associated peripheral devices and microprocessor 118. For example, keyboard 134 which may be a conventional keyboard is connected to adapter 132B to provide manually generated data input to the microcomputer 116.

Additional memory is provided by disk drive 136 (for example, a type SA900/901 diskette storage drive) which is connected to an appropriate interface such as a disk controller card 138. In one embodiment, card type M68KVM21 manufactured by Motorola was employed. Card 138 connects with adapter 132C to allow microprocessor 118 to transfer data through the adapter 132C and the interface 138 to be stored/recalled by drive 136. In some embodiments, microcomputer 116 (except for perhaps the display 130) can be purchased as a microcomputer package. For example, a model uMAC-4000 measurement and control system manufactured by Analog Devices can be used to collect analog data directly and to exchange digital data at various input/output ports. Alternatively, the foregoing microcomputer system can be upgraded to include the apparatus known as the Macsym 350 computerized measurement and control system also manufactured by Analog Devices.

Printer 140 may be a Seiko type AN-101F printer. Its interface 142 may employ the integrated interface circuit type MC74452 manufactured by Motorola as described in the application literature published by Seiko. Interface 142 also connects to a port of adapter 132E so that data originating from microprocessor 118 can flow through adapter 132E interface 142 and drive printer 140.

The other interfaces 144A-144E are of two types, depending upon whether the data being transferred is analog or digital. For channels in which analog data is being conveyed, an analog to digital and digital to analog converter is employed. For example, in interface 144E the associated temperature monitors 146 comprise the analog thermistors 78, 94 and 100 of FIG. 5. As previously described in connection with FIG. 2, temperature monitors 146 can include a bridge driving a differential amplifier or alternatively, the conditioners models 2B30 and/or 2B31 manufactured by Analog Devices. In the preferred embodiment, interface 144E is the only analog channel. In embodiments where more than one analog channel is required, an analog to digital and a digital to analog converters can be connected to a multiplexer to reduce the need to have several duplicate converters. Interface 144E has a parallel output connected to chart recorder 148 for keeping a real time record of the variations of the temperature monitors 146.

The interfaces 144A-144D handle primarily digital data. For example, the positioning information from subsystem 150 are signals derived by the various indexing limit switches (switches 115 and 117 of FIGS. 5 and 6). Accordingly, interface 144A need only have D-type flip flops (not shown) to store the current state of the various switch type devices connected thereto. Similarly, heater 152, which corresponds to the heating coil 76 of FIG. 5, is either on or off and therefore digital in nature in this embodiment. Therefore, interface 144A incorporates a separate D-type flip flop (not shown) which drives a relay (not shown) to control the heater 152. In those embodiments, however, where the drive to heater 152 is proportional, the analog/digital converters of block 144E can be employed in interface 144A.

Fail safe sensors 154 are also preferably of a digital nature so that interfaces 144B and 144C need only contain D-type flip flops (no shown) and, as required, relays (not shown). Sensors 154 may include microswitches to assure that positioning means 108 of FIG. 5 is within certain limits and/or is at initial position appropriate for starting the next cycle. Sensors 154 may also include thermal switches that are in an on/off state depending upon whether the measured temperature is above/below a desired temperature. The latter thermal switch would correspond to sensor 74 of FIG. 5, also referred to as a stabilizing sensor. (In some embodiments, this function may be performed by the temperature sensor associated with the reagent or wash fluid.) Fail safe sensors 154 may also include flow measuring instruments to verify that a flow demanded by a pump is occurring or has ceased, as appropriate. Block 156 constitutes the pumps and valves associated with the reagent and wash as shown in FIG. 5, for example, pumps 88 and 96.

To facilitate an understanding of the principles associated with the apparatus of FIGS. 4-8, its operation will now be briefly described in conjunction with the flow chart of FIG. 9. The flow chart of FIG. 9 represents a broad description of the programming contained within the microcomputer 116. This program may be contained in read only memories 128A and 128B. The apparatus is initially set-up by filling the wash bottle 92 (FIG. 5) and the reagent bottles 98 with the appropriate liquids. For example, if a sensitivity test is being performed reagent bottles 98 may be filled with various antibiotics. Alternatively, the reagent bottles 98 can be filled with a growth-inducing reagent to determine the metabolic characteristics of microorganisms suspended in the test tubes of tray 104. In the event that only four different reagents are being used, the nineteen stations in each row of tray 104 may be partitioned into four groups of four. One of the remaining three positions may be filled with a fluid that is used as a control sample for measuring a control temperature. However, the system can be loaded to perform up to nineteen different tests for each row of the tray 104. Normally successive rows contain different samples.

Thereafter, the lid 62 and doors 64 are closed to allow temperatures to reach an equilibrium. The microcomputer 116 can be started immediately although it may be preferable to wait an additional period of time to allow temperatures to stabilize. In any event, upon the starting of the program, (step ST1 of FIG. 9) control decisions are made at step ST2 wherein a decision is made as to which one of three brances is to be taken. The first branch taken is the one leading to step ST3 wherein the temperature of the water within panels 60 and 61 (FIG. 5) are measured by means of sensor 74. In FIG. 8, such measurement is relayed from block 154 through interface 144B and adapter 132D to microcomputer 116. Once measured, the signal (which may be a go/no go signal or an analog signal) is compared to the desired result in step ST4. If the measured value is incorrect, the bath heater is adjusted at step ST5 by issuing a control signal through adapter 132G (FIG. 8) and interface 144A to turn on heater 152 (also shown as heating coil 76 in FIG. 5). Note that in some embodiments, an excessive bath temperature may be indicated in step ST4 in which case (FIG. 9) the heater will be turned off at step ST5. Step ST5 is then followed by step ST3 which repeats the cycle until a proper bath temperature is observed at step ST4. Thereafter, the program control is returned to the control cycler at step ST2.

The control cycler at step ST2 now initiates the branch commencing at step ST6. In step ST6 data is gathered from monitors at block 146 (FIG. 8) and monitors 146 may include, for that purpose, a separate thermistor (not shown) for measuring the air temperature within the housing of FIG. 4A. Preferably however, the air ambient temperature can be measured through probe 78 (FIG. 6) which at this time, is not immersed in a sample 102. Next, in step ST7, data gathered from the monitors of block 146 (FIG. 8) are compared against desired values of reagent and wash temperature using probe 94 and 100 (FIG. 5). In step ST8 the just measured temperatures are compared to predetermined target temperatures. If any of the measured signals do not fall within the desired range, steps ST6-ST8 are repeated until a proper equilibrium is reached. the temperature should fall within the desired range. Once stable and correct temperatures are achieved, control is returned to cycler step ST2.

In some embodiments the branches starting with step ST3 and ST6 may be repeated one more time to determine that the temperatures remain correct. Also in such embodiments, the heaters associated with step ST5 may be turned off to insure that no thermal shocks are caused during the critical measurement steps which follow. Accordingly, the control cycler at step ST2 now transfers control to step ST9 wherein positioning means 108 (FIG. 5) is activated to raise platform 106 so that probe 78 is inserted into the first row of samples 102 in tray 104. The vertical lifting of platform 106 continues until limit switch 117 determines that the height is correct. In FIG. 8, the command to lift the table is conveyed through components 132G and 144A while the indication that the correct height has been reached is conveyed in the reverse direction. Thereafter, microcomputer 116 at step ST10 (FIG. 9) measures the output of the sample sensor 78 (FIG. 5) by conveying a measurement signal issued through interface 144E and adapter 132K to microcomputer 116 (FIG. 8). In this step ST10, there may be a delay of several minutes to confirm that the temperatures are stable. Once stabilization is confirmed, step ST11 is executed to commence reagent injection. Accordingly, the microcomputer 116 (FIG. 8) issues a signal through adapter 132H and interface 144D to command the pumps 96 (FIG. 5) to operate for a predetermined period of time. Accordiingly, reagents from bottles 98 flow through pumps 96 to reagent tube 84 to inject into test container 102 a predetermined amount of reagent. Next, in step ST12 the temperature of the sample is remeasured in a fashion similar to step ST10. In step ST12 however, a differential or balanced measurement can be made by comparing the sample temperature to another reference temperature. For example, there may be in the nineteenth position in each row of tray 104, a sample which consists of distilled water and the inserted reagent is also distilled water. Thus, any temperature change occuring in this controlled sample is due to thermal effects unconcerned with organism metabolism. Alternatively, the sample temperature can be referenced to that measured by either reagent sensor 100 or wash sensor 94. In some embodiments, additional sensors may be employed to reference the sample measurements to the temperature within the water jacket 60 and 61. After a preprogrammed amount of time, step ST13 is executed wherein the monitored data is stored in memory and optionally printed through printer 140 (FIG. 8). Next, in step ST14 (FIG. 9), the positioning means 108 (FIG. 5) is actuated to lower platform 106 by energizing motor M2. After step ST14 when the probe 78 has been lifted from the sample, a wash cycle is started, as indicated at step ST 15. Accordingly, the wash pump 88 (FIG. 5) is energized for a period of time to cause a flow of wash fluid through tube 86 and around probe 78 which will then drip into the just measured test tubes 102. Thereafter, motor M1 is energized to index the platform 106 to the next position (step ST14) as determined when the next cam 113 (FIGS. 5 an 6) reaches limit switch 115. In FIG. 8 this data transfer is provided through components 132G, 144A and 150. Thereafter, step ST16 passes control back to control cycler at step ST2.

It may be desirable at this point for the control cycler to reexecute the branches of steps ST3 and ST6 to confirm that the bath, chamber reagent and wash temperatures are all within tolerable ranges. In any event, the loop starting with step ST9 is executed again wherein the probe 78 is inserted into the next row of samples and the temperature measurements previously described are taken again. In this fashion, the loop of step of ST9 is repetitively performed until at step ST 15 the number of cycles has reached the preprogrammed amount. Thereafter, the program ends as indicated as step ST16.

It will be appreciated that various modifications can be made to the above described apparatus. As previously described, the system can be operated by either an analog or digital controller. For use in the more elaborate arrangement of FIG. 5, an analog controller could employ various timers and threshold detectors to control the process. The output measurements could be produced on a printer or a strip chart recorder of sufficient sensitivity which may be then be interpreted by the operator. It is expected that the programming described in the flow chart of FIG. 9 can be rearranged to produce different steps or to arrange the steps in a different order. While various integrated circuits have been disclosed, it will be understood that circuits using discrete components can be employed as needed. Also, while a two dimensional array of samples has been disclosed, a single file or other arrangement of samples can be employed. Additionally, while the samples are raised to the probes in this embodiment, there is no reason why probes cannot be lowered to the samples and thereafter indexed horizontally to service successive rows. It will be understood that the housing may take various forms and need not have a water jacket but may employ instead an internal heater. Furthermore, it is to be understood that the times allowed for temperature changes due to metabolic effects can be altered depending upon the relevant biochemistry and the relevant structure. Also, while limit switches are disclosed as the means of controlling the positioning means, in some embodiments synchros or other equivalent apparatus can be used to position the table in a feedback arrangement. Also, the various dimensions and proportions illustrated herein are merely exemplary and may vary depending upon the size and number of the samples, the desired thermal insulation, the speed of operation, the structural integrity required, etc.

Obviously, many modifications and variations of the present invention are possible in light of the above teachings. It is, therefore, to be understood that within the scope of the appended claims, the invention may be practiced otherwise than as specifically described.

What is claimed is:

1. A tester for determining a metabolic characteristic of microorganisms suspended in a medium comprising:
   a housing means having an internal ambient temperature;
   a reagent supply mounted in said housing means and containing a quantity of at least one test reagent; a probe means mounted in said housing means and sized to be inserted into said medium, there existing a probe temperature at said probe means, said probe means providing a reaction signal signifying the probe temperature at said probe means;
   a dispensing means coupled between said reagent supply and said probe means for delivering at the probe means from the reagent supply said test reagent;
   reference means mounted in said housing means for providing a reference signal responsive to said ambient temperature, said reference means being spaced from said probe means to preclude insertion into said medium; and
   control means coupled to said probe means, said reference means and said dispensing means for controlling the amount of said test reagent dispensed by said dispensing means and for indicating the relative variation between said reaction signal and said reference signal after delivery of said test reagent at said probe means.

2. A tester according to claim 1 further comprising:
   a wash supply containing a quantity of wash fluid; and
   providing means coupled between said wash supply and said probe means for providing a cleansing flow of said wash fluid upon said means after delivery of said test reagent at said probe means.

3. A tester according to claim 2 further comprising:
positioning means for causing relative motion between said medium and said probe means and for causing the probe means to be inserted into the medium for an interval of time, said positioning means having a first means for supporting said medium and a second means for supporting said probe means, said positioning means being operable to move relatively said first and second means.

4. A tester according to claim 3 wherein said control means is coupled to said positioning means for operating it sequentially with said dispensing means.

5. A tester according to claim 4 wherein said medium is partitioned into a plurality of samples and wherein said probe means comprises:
a plurality of reaction sensors each coupled to said control means, there existing a reaction temperature at each of said reaction sensors, said reaction sensors each providing a signal signifying the reaction temperature at each of said reaction sensors, said reaction sensors being spaced to be separately insertable into a corresponding one of said samples to measure the reaction temperature of each.

6. A tester according to claim 5 wherein said reagent supply comprises a plurality of reservoirs and wherein said dispensing means comprises:
a plurality of regulators each coupled to a respective one of said reservoirs for dispensing a predetermined amount of its contents to an associated one of said plurality of reaction sensors.

7. A tester according to claim 6 wherein each of said reaction sensors includes:
a reagent tube mounted on its associated one of said reaction sensors for releasing at said associated one of said reaction sensors the reagent dispensed by said dispensing means; and
a wash tube mounted alongside said reagent tube for releasing the wash fluid dispensed by said providing means.

8. A tester according to claim 1 wherein said housing means contains a stabilizing liquid and is operable to encompass and support said medium.

9. A tester according to claim 8 further comprising:
a stabilizing sensor coupled to said housing means for providing a stabilizing signal signifying the temperature of said stabilizing liquid, said control means being coupled to said stabilizing sensor for providing a signal signifying the difference between said stabilizing signal and a pre-determined value, said predetermined value being established to keep said ambient temperature at a magnitude that promotes reaction by said test reagent in said medium.

10. A tester according to claim 4 wherein said control means is connected to said positioning means to initiate insertion of said probe means into said medium, followed by injection of said reagent by said dispensing means.

11. A tester according to claim 10 wherein said positioning means comprises:
a platform being arranged relative to said probe means for freedom of motion in a horizontal direction, said platform being arranged to support said medium as a plurality of separate samples arranged in at least one column along said horizontal direction, said platform being arranged to reciprocate relative to said probe means, wherein relative reciprocation of said probe means and said platform are sized to insert and remove said probe means from said medium, said control means being operable to control said platform and to insert said probe means into successive ones of said samples in said column.

12. A tester according to claim 11 wherein said control means is operable to inititate said providing means before inserting said probe means into the next one of the samples in said column.

13. A tester according to claim 1 wherein said housing means contains a stabilizing liquid and is operable to encompass and support said medium.

14. A tester according to claim 12 wherein said housing means contains a stabilizing liquid and is operable to encompass and support said medium.

15. A tester according to claim 1 wherein said reference means comprises:
a reagent sensor coupled to said reagent supply for providing a reagent signal signifying the temperature at said reagent supply.

16. A tester according to claim 15 wherein said control means is coupled to said reagent sensor to initiate operation of said positioning means in response to said reagent signal.

17. A tester according to claim 15 wherein said control means is operable to record said reaction signal of said probe means relative to said reagent signal as time elapses.

18. A tester according to claim 8 wherein said housing means comprises:
a box having at least one wall and at least one door, said wall having a predetermined thickness, said wall having a cavity within said wall, said cavity being liquid-tight and having means for filling said cavity with a liquid.

19. A tester according to claim 12 wherein said control means comprises:
a digital processor coupled to said providing means, said positioning means, said dispensing means and said probe means for monitoring the probe means and controlling the other; and
memory means coupled to said digital processor processing means for storing data obtained by it.

* * * * *